US009959561B2

(12) United States Patent
Reed et al.

(10) Patent No.: US 9,959,561 B2
(45) Date of Patent: May 1, 2018

(54) SIMPLENUTRITION NUTRITIONAL MANAGEMENT SYSTEM

(71) Applicant: Safeway Inc., Pleasanton, CA (US)

(72) Inventors: Margaret-Ann Reed, Pleasanton, CA (US); John Calvert, Pleasanton, CA (US); Steve Moylan, Pleasanton, CA (US)

(73) Assignee: Safeway Inc., Pleasanton, CA (US)

( * ) Notice: Subject to any disclaimer, the term of this patent is extended or adjusted under 35 U.S.C. 154(b) by 659 days.

(21) Appl. No.: 13/837,907

(22) Filed: Mar. 15, 2013

(65) Prior Publication Data
US 2013/0226729 A1 Aug. 29, 2013

Related U.S. Application Data

(63) Continuation of application No. 13/537,666, filed on Jun. 29, 2012.
(Continued)

(51) Int. Cl.
G06Q 30/06 (2012.01)
G06Q 30/02 (2012.01)
G09B 19/00 (2006.01)

(52) U.S. Cl.
CPC ..... G06Q 30/0631 (2013.01); G06Q 30/0226 (2013.01); G09B 19/0092 (2013.01)

(58) Field of Classification Search
CPC .................................................. G06Q 30/0631
(Continued)

(56) References Cited

U.S. PATENT DOCUMENTS 3,959,624 A 5/1976 Kaslow
4,124,109 A 11/1978 Bissell et al.
(Continued)

FOREIGN PATENT DOCUMENTS

CA 2603479 A1 4/2008
CA 2620462 A1 11/2008
(Continued)

OTHER PUBLICATIONS

Decision on Appeal dated Jul. 7, 2015 (7 pages), U.S. Appl. No. 11/560,930, filed Nov. 17, 2006.
(Continued)

*Primary Examiner* — Alexis Casey
(74) *Attorney, Agent, or Firm* — Conley Rose, P.C.; Rodney B. Carroll

(57) ABSTRACT

A nutritional management system which comprises a processor, a memory, a first data store comprising a list of products, universal product codes associated with the products, and nutritional information associated with the products, a second data store comprising a physiological information profile for each of a plurality of different loyalty card users, an application stored in the memory. When executed by the processor the application accesses the second data store to read the physiological information profile of a loyalty card user, analyzes the physiological information profile based on objective nutritional guidelines set forth for physiological characteristics disclosed in the physiological information profile, searches the first data store to find products that satisfy the objective nutritional guidelines, transmits the products, receives a selection of one or more of the products, and promotes generating a personalized shopping list comprising selected products that is based on the physiological information profile.

12 Claims, 6 Drawing Sheets

Related U.S. Application Data

(60) Provisional application No. 61/504,036, filed on Jul. 1, 2011, provisional application No. 61/665,787, filed on Jun. 28, 2012.

(58) Field of Classification Search
USPC .................................................. 705/26.7
See application file for complete search history.

(56) References Cited

U.S. PATENT DOCUMENTS

| | | | |
|---|---|---|---|
| 4,412,631 A | 11/1983 | Haker | |
| 4,554,446 A | 11/1985 | Murphy et al. | |
| 4,674,041 A | 6/1987 | Lemon et al. | |
| 4,723,212 A | 2/1988 | Mindrum et al. | |
| 4,882,675 A | 11/1989 | Nichtberger et al. | |
| 5,233,520 A * | 8/1993 | Kretsch .............. | G01G 19/4146 128/921 |
| 5,412,560 A | 5/1995 | Dennision | |
| 5,412,564 A * | 5/1995 | Ecer ...................... | G06F 19/323 128/921 |
| 5,649,114 A | 7/1997 | Deaton et al. | |
| 5,819,735 A | 10/1998 | Mansfield et al. | |
| 5,857,175 A | 1/1999 | Day et al. | |
| 5,940,818 A | 8/1999 | Malloy et al. | |
| 6,003,024 A | 12/1999 | Bair et al. | |
| 6,123,259 A | 9/2000 | Ogasawara | |
| 6,533,173 B2 | 3/2003 | Benyak | |
| 6,817,863 B2 * | 11/2004 | Bisogno .................. | A23L 1/293 235/375 |
| 6,965,868 B1 | 11/2005 | Bednarek | |
| 6,975,910 B1 | 12/2005 | Brown et al. | |
| 6,980,999 B1 | 12/2005 | Grana | |
| 7,090,638 B2 * | 8/2006 | Vidgen ............... | G06F 19/3475 128/921 |
| 7,213,743 B2 | 5/2007 | Carlson et al. | |
| 7,783,566 B2 | 8/2010 | Armes et al. | |
| 8,398,546 B2 | 3/2013 | Pacione et al. | |
| 8,626,796 B2 | 1/2014 | McBride et al. | |
| 8,631,050 B1 | 1/2014 | Gayle | |
| 2001/0014868 A1 | 8/2001 | Herz et al. | |
| 2003/0171944 A1 * | 9/2003 | Fine ........................ | G06Q 30/06 705/2 |
| 2003/0208383 A1 | 11/2003 | Hauck et al. | |
| 2004/0210549 A1 | 10/2004 | Tarbet | |
| 2005/0010476 A1 | 1/2005 | Combs | |
| 2005/0027174 A1 | 2/2005 | Benardot | |
| 2005/0042582 A1 * | 2/2005 | Graves ............... | G09B 19/0092 434/127 |
| 2005/0113649 A1 * | 5/2005 | Bergantino ............ | G06Q 50/22 600/300 |
| 2005/0113650 A1 * | 5/2005 | Pacione ................. | A61B 5/411 600/300 |
| 2005/0160014 A1 | 7/2005 | Moss et al. | |
| 2006/0263750 A1 | 11/2006 | Gordon | |
| 2008/0086373 A1 | 4/2008 | Aitken et al. | |
| 2008/0086374 A1 | 4/2008 | Aitken et al. | |
| 2010/0177100 A1 * | 7/2010 | Carnes ................ | G06F 19/3456 345/440 |
| 2012/0310758 A1 | 12/2012 | Bai et al. | |

FOREIGN PATENT DOCUMENTS

| | | | |
|---|---|---|---|
| WO | 8501373 A1 | 3/1985 | |
| WO | 9923585 A1 | 5/1999 | |

OTHER PUBLICATIONS

Foreign communication from a related counterpart application—Canadian Office Action, Application No. 2,603,479, dated Oct. 20, 2014, 4 pages.
Office Action dated Dec. 17, 2014 (32 pages), U.S. Appl. No. 11/749,672, filed May 16, 2007.
Office Action dated Apr. 8, 2014 (26 pages), U.S. Appl. No. 11/749,672, filed May 16, 2007.
Examiner's Answer dated Aug. 1, 2012 (6 pages), U.S. Appl. No. 11/560,930, filed Nov. 17, 2006.
Advisory Action dated Jul. 9, 2009, 3 pages, U.S. Appl. No. 11/749,672, filed May 16, 2007.
Advisory Action dated Jul. 28, 2009, 3 pages, U.S. Appl. No. 11/560,930, filed Nov. 17, 2006.
Advisory Action dated Apr. 23, 2010, 3 pages, U.S. Appl. No. 11/749,672, filed May 16, 2007.
Office Action dated Sep. 4, 2009, 16 pages, U.S. Appl. No. 11/560,930, filed Nov. 17, 2006.
Office Action (Final) dated May 6, 2009, 16 pages, U.S. Appl. No. 11/560,930, filed Nov. 17, 2006.
Office Action dated Nov. 4, 2008, 15 pages, U.S. Appl. No. 11/560,930, filed Nov. 17, 2006.
Office Action (Final) dated Apr. 29, 2009, 15 pages, U.S. Appl. No. 11/749,672, filed May 16, 2007.
Office Action dated Nov. 5, 2008, 16 pages, U.S. Appl. No. 11/749,672, filed May 16, 2007.
Office Action dated Aug. 6, 2009, 19 pages, U.S. Appl. No. 11/749,672, filed May 16, 2007.
Office Action (Final) dated Feb. 24, 2010, 17 pages, U.S. Appl. No. 11/749,672, filed May 16, 2007.
Office Action (Final) dated Mar. 25, 2010, 17 pages, U.S. Appl. No. 11/560,930, filed Nov. 17, 2006.
Office Action dated Jun. 22, 2010, 21 pages, U.S. Appl. No. 11/749,672, filed May 16, 2007.
Office Action dated Jul. 22, 2010, 23 pages, U.S. Appl. No. 11/560,930, filed Nov. 17, 2006.
Office Action dated Nov. 10, 2010, 18 pages, U.S. Appl. No. 11/560,930, filed Nov. 17, 2006.
Office Action (Final) dated Dec. 8, 2010, 25 pages, U.S. Appl. No. 11/749,672, filed May 16, 2007.
Office Action (Final) dated Mar. 31, 2011, 19 pages, U.S. Appl. No. 11/560,930, filed Nov. 17, 2006.
Office Action dated Jun. 14, 2011, 27 pages, U.S. Appl. No. 11/749,672, filed May 16, 2007.
Filing receipt and specification for patent application entitled "Nutrition management and meal planning program," by Stuart W. Aitken, et al., filed Oct. 6, 2006 as U.S. Appl. No. 60/828,495.
Filing receipt and specification for patent application entitled, "SimpleNutrition Nutritional Management System," by Margaret-Ann Reed, et al., filed Jul. 1, 2011 as U.S. Appl. No. 61/504,036.
Filing receipt and specification for patent application entitled, "SimpleNutrition Nutritional Management System," by Margaret-Ann Reed, et al., filed Jun. 28, 2012 as U.S. Appl. No. 61/665,787.
Filing receipt and specification for patent application entitled, "SimpleNutrition Nutritional Management System," by Margaret-Ann Reed, et al., filed Jun. 29, 2012 as U.S. Appl. No. 13/537,666.
Advisory Action dated May 3, 2012, 2 pages, U.S. Appl. No. 11/749,672, filed May 16, 2007.
Office Action (Final) dated Jan. 20, 2012, 23 pages, U.S. Appl. No. 11/749,672, filed May 16, 2007.
Foreign communication from a related counterpart application—Canadian Office Action, Application No. 2,620,462, dated Jan. 29, 2015, 5 pages.
Office Action (Final) dated Apr. 7, 2016 (54 pages), U.S. Appl. No. 11/749,672, filed May 16, 2007.
Office Action dated Nov. 6, 2015 (40 pages), U.S. Appl. No. 13/537,666, filed Jun. 29, 2012.
Office Action dated Feb. 10, 2016 (19 pages), U.S. Appl. No. 11/560,930, filed Nov. 17, 2006.
Office Action (Final) dated May 24, 2016 (24 pages), U.S. Appl. No. 13/537,666, filed Jun. 29, 2012.
Office Action (Final) dated Jun. 30, 2016 (9 pages), U.S. Appl. No. 11/560,930, filed Nov. 17, 2006.
Office Action dated Feb. 10, 2017 (20 pages), U.S. Appl. No. 13/537,666, filed Jun. 29, 2012.
Office Action dated Sep. 14, 2017 (41 pages), U.S. Appl. No. 11/749,672, filed May 16, 2007.

(56) References Cited

OTHER PUBLICATIONS

Office Action (Final) dated Sep. 22, 2017 (21 pages), U.S. Appl. No. 13/537,666, filed Jun. 29, 2012.

* cited by examiner

SIMPLENUTRITION NUTRITIONAL MANAGEMENT SYSTEM

CROSS-REFERENCE TO RELATED APPLICATIONS

This application is a continuation application of, and claims priority to, U.S. patent application Ser. No. 13/537,666 filed Jun. 29, 2012, titled "SimpleNutrition Nutritional Management System," which claims priority to U.S. Provisional Application Ser. Nos. 61/504,036, filed Jul. 1, 2011, and 61/665,787, filed Jun. 28, 2012, both entitled "SimpleNutrition Nutritional Management System," by Margaret-Ann Reed, et al., each of which is incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Loyalty cards have become increasingly common in grocery stores. Discounts may be offered in grocery stores based on the presentation of loyalty cards at check-out. Information about shopping behavior may be collected based on loyalty cards and analyzed to provide improved stocking of products. Shoppers are becoming more aware of the healthfulness of the foods that they buy. Foods that fulfill like eating and/or meal planning purposes may nonetheless differ in their healthfulness. Unfortunately, many shoppers may wish to eat healthily and/or to feed their families healthy food, but may be insufficiently knowledgeable about which foods are healthier than others and/or may not have time to research the nutritional differences among foods.

SUMMARY

In an embodiment, a nutritional management system is disclosed. The system comprises a processor, a memory, a first data store comprising a list of products, universal product codes associated with the products, and nutritional information associated with the products, a second data store comprising purchase histories linked to a plurality of different loyalty card users, and an application stored in the memory. When executed by the processor, the application accesses the second data store to read a purchase history of a loyalty card user over a most recent predefined time period, analyzes a most recent predefined time period of the purchase history of the loyalty card user based on objective nutritional guidelines to identify a predefined number of most unhealthy purchased items, searches the first data store to find substitutes for the unhealthy purchased items, transmits the substitutes, receives a selection of one or more of the substitutes, and promotes generating a shopping list comprising selected substitutes.

In an embodiment, a computer based method of shopping for food is disclosed. The method comprises accessing a first data store to read a most recent predefined time period of purchase history of a loyalty card user, wherein the first data store comprises purchase histories linked to a plurality of different loyalty card users, analyzing the food items of the most recent predefined time period of purchase history based on objective nutritional guidelines to identify a predefined number of the most unhealthy purchased items, and identifying a list of potential product substitutes by accessing a second data store comprising a list of products, universal product codes associated with the products, and nutritional information associated with the products to obtain a list of product entries that belong to the same food types as the unhealthy purchased items. The method further comprises identifying a list of candidate product substitutes by analyzing the list of potential product substitutes based on the objective nutritional guidelines, presenting the list of candidate substitutes, receiving substitute selections, and transmitting a shopping list comprising the substitute selections.

In an embodiment, a computer based method of shopping for food is disclosed. The method comprises accessing a first data store to read a most recent predefined time period of purchase history of a loyalty card user, wherein the first data store comprises purchase histories linked to a plurality of different loyalty card users, receiving a selection of a food category filter criteria and a selection of a first food nutrient filter criteria, and presenting a list of the products purchased during the most recent predefined time period that match the food category filter criteria selection. The method further comprises receiving a selection of one of the products that match the food category filter criteria selection, accessing a second data store to identify products that match the food category filter criteria selection, wherein the second data store comprises a list of products, universal product codes associated with the products, and nutritional information associated with the products, and analyzing the products in the second data store that match the food category filter based on the first food nutrient filter criteria to identify substitution candidates. The method further comprises presenting the nutritional information associated with the selected product from the most recent predefined time period of purchase history side-by-side with nutritional information associated with at least one substitute candidate, receiving a substitute selection, and transmitting a shopping list comprising the substitute selection.

In an embodiment, a nutritional management system is disclosed. The nutritional management system comprises a processor, a memory, a first data store comprising a list of products, universal product codes associated with the products, and nutritional information associated with the products, a second data store comprising a physiological information profile for each of a plurality of different loyalty card users, and an application stored in the memory that, when executed by the processor, accesses the second data store to read the physiological information profile of a loyalty card user, analyzes the physiological information profile of the loyalty card user based on objective nutritional guidelines set forth for one or more physiological characteristics disclosed in the physiological information profile of the loyalty card user, searches the first data store to find products that satisfy the objective nutritional guidelines, transmits the products, receives a selection of one or more of the products, and promotes generating a personalized shopping list comprising selected products that is based on the loyalty card user's physiological information profile.

In an embodiment, a computer based method of shopping for food is disclosed. The method comprises accessing a first data store to read a physiological information profile for a loyalty card user, analyzing the physiological information profile based on objective nutritional guidelines set forth for one or more physiological characteristics disclosed in the physiological information profile of the loyalty card user to identify products that satisfy the objective nutritional guidelines, identifying a list of products that satisfy the objective nutritional guidelines by accessing a second data store comprising a list of products, universal product codes associated with the products, and nutritional information associated with the products, presenting the list products that satisfy the objective nutritional guidelines, receiving product selections, and transmitting a shopping list comprising the product selections.

In an embodiment, a computer based method of shopping for food is disclosed. The method comprises receiving a selection of a food category filter criteria, a selection of a first food nutrient filter criteria, and a selection of a first food attribute filter criteria, accessing a first data store to identify products that match the food category filter criteria selection, wherein the first data store comprises a list of products, universal product codes associated with the products, nutritional information associated with the products, and attributes of the products, analyzing the products in the first data store that match the food category filter criteria based on the first food nutrient filter and the first food attribute filter to identify products that satisfy the filter criteria, presenting the nutritional information and attributes associated with the identified products, receiving a selection of one or more products, and transmitting a shopping list comprising the selected products.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Figure 1:
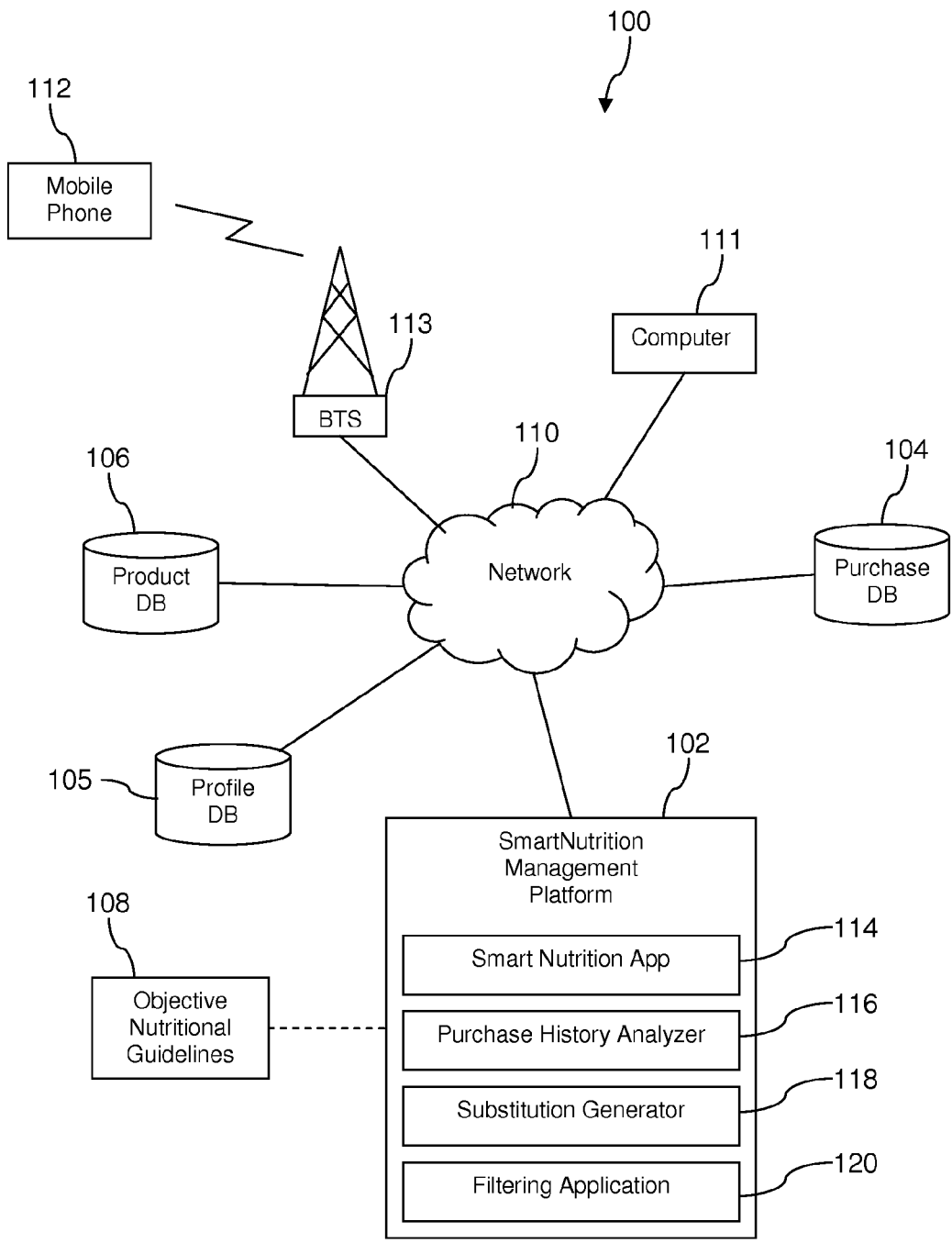
FIG. 1 is a block diagram of a nutritional management system according to an embodiment of the disclosure.

Turning now to FIG. 1, a nutritional management system 100 is described. In an embodiment, the system 100 comprises a SimpleNutrition management platform 102, a customer purchase data store 104, a physiological information profile data store 105, a product data store 106, a repository of objective nutritional guidelines 108, and a network 110.

The system 100 may further comprise a plurality of computers 111, a plurality of mobile phones 112, and a plurality of base transceiver stations (BTSs) 112. The network 110 comprises one or more public networks, one or more private networks, or a combination thereof. The SimpleNutrition management platform 102, herein after referred to as the platform 102, may comprise a computer system. Computer systems are described in more detail hereinafter. While a mobile phone 112 is illustrated in FIG. 1 and described below, it is understood that the mobile phone 112 may be substituted for by a personal digital assistant (PDA) or by a media player in some embodiments.

The platform 102 provides a number of tools for assisting a customer, for example a grocery store loyalty card user or club card user, to build a shopping list for shopping in a grocery store while guiding the customer to make more healthy food choices. In an embodiment, the platform 102 executes a simple nutrition application 114, a purchase history analyzer 116, a substitution generator 118, and a filtering application 120. One skilled in the art will appreciate that in an embodiment, two or more of the components 114, 116, 118, or 120 may be combined together and/or that one or more of the components 114, 116, 118, 120 may be split into two or more separate components. It is understood that the platform 102 may execute other applications. For example, in an embodiment, the platform 102 may further execute a meal planning application. For more details about meal planning applications, see U.S. patent application Ser. No. 11/560,930, filed Nov. 17, 2006, published as U.S. Publication of Application No. 2008/0086373 A1 and entitled "Nutrition Management and Meal Planning," by Stuart W. Aitken, et al., which is hereby incorporated by reference in its entirety.

The purchase data store 104 comprises data about items purchased by a plurality of customers, for example purchases by customers at any of a plurality of stores operated by a grocery store chain or, alternatively, at a specific store operated by a grocery store chain. The data may comprise an identification of the purchasing customer, a universal product code (UPC) that identifies each purchased item, a quantity and/or weight, a date and time of the purchase, and other related information. The identification of the purchasing customer may be a loyalty card identity or a club card identity. In an embodiment, the purchasing customer may receive loyalty card discounts which may be associated with purchase history. The data may be stored as individual purchase items or as individual items grouped by check-out session or grouped in some other manner. The data may extend back a predefined period of time, for example about three months, about six months, about nine months, about a year, about a year and a half, about two years, or some other predefined period of time. The predefined period of time need not be defined as an integer number of months, but may be defined in number of days, number of weeks, or some other time unit. Alternatively, the data may extend back indefinitely, for example to a first ever purchase by a loyalty card user.

The physiological information profile data store 105 may comprise physiological information profiles for a plurality of different loyalty card users. The physiological information contained in the physiological information profiles may comprise physical attributes and/or characteristics such as a loyalty card user's height, weight, race, sex, age, body fat percentage, BMI, caloric expenditure, allergies, or other physical characteristics. Additionally, the physiological information contained in the physiological information profiles may comprise medical information relating to the loyalty card user such as the loyalty card user's history of injuries, history of illness, organ information, immune system function, family medical history, personal medical history, current medical condition, addictions, dental health, gastrointestinal health, mental health, joint health, cardiovascular health, respiratory health, hormone activity, history of infection, history of disease, information about medication that the loyalty card user is taking, or information about another aspect of the loyalty card user's physiological and/or medical conditions.

The physiological information profiles contained in the physiological information profile data store 105 may be updated by their corresponding loyalty card user. In an embodiment, the loyalty card user may access his/her corresponding physiological information profile and complete a questionnaire, answer medical questions, or supply information as he/she chooses. Alternatively, the physiological information may be provided in another manner. The information contained a loyalty card user's physiological information profile may be ranked in order of precedence by the user or by a predetermined ranking system. For example, a medical condition such as diabetes may be given precedence over a physical characteristic such as height. The information may be ranked as it is entered in the physiological information profile, after it is entered in the physiological information profile, or at some other time.

The product data store 106 may comprise data about products that are offered for sale by the subject grocery store or grocery store chain. It is understood that in some circumstances the product data store 106 may comprise data about products that are not offered for sale, for example products that have been discontinued but have not yet been removed from the product data store 106 or may comprise data about products that are planned to be offered for sale in the future. The data may comprise an identity of the product, such as a universal product code, a manufacturer of the product, product shelf price and/or promotion price information, and nutritional information about the product. The nutritional information may comprise a quantity of calories, protein, carbohydrate, fat, saturated fat, trans fat, fiber, cholesterol, sodium, potassium, calcium, iron, iodine, selenium, vitamin A, vitamin C, Vitamin D, sugar, folate, B vitamins, and other nutrients that are contained in the subject product. The nutritional information may comprise indications of percentage of daily recommended amounts of nutrients provided by the subject product. While illustrated in FIG. 1 and described separately, in an embodiment, the data stores 104, 105, and 106 may be combined in a single data store.

The objective nutritional guidelines 108 comprise one or more sources of information on nutritional guidelines promulgated by independent groups, for example the United States Department of Agriculture nutritional guidelines, the Food and Drug Administration nutritional guidelines. The nutritional guidelines may be provided by other governmental organizations or by private medical and/or nutritional organizations, for example by the American Medical Association or some other organization. The use of the term "objective" in "objective nutritional guidelines" is meant to convey that the guidelines are provided by presumably independent sources that are customarily granted a presumption of disinterested competence on nutritional matters.

The objective nutritional guidelines 108 may comprise recommended daily values for nutrients, minerals, vitamins, and/or other dietary substances. Additionally, the objective nutritional guidelines 108 may comprise maximum thresholds for consumption of deleterious nutrients or foods as well as minimum thresholds for consumption of nutrients or foods. For example, the guidelines may comprise a maximum quantity of canned Albacore tuna per month and a minimum quantity of protein per day. Albacore tuna may contain elevated levels of mercury, a harmful ingredient when consumed in excessive amounts.

The objective nutritional guidelines 108 may be variable based on a loyalty card user's physiological characteristics disclosed in the loyalty card user's physiological information profile. For example, the recommended daily values, maximum thresholds, and minimum thresholds may be higher for a larger, robust loyalty card user than for a smaller, less robust loyalty card user. The objective nutritional guidelines 108 for a loyalty card user may take into account the plurality of physiological information discussed hereinabove with reference to the physiological information profile data store 105. Accordingly, the objective nutritional guidelines 108 for a loyalty card user with diabetes may be different than the objective nutritional guidelines 108 for a non-diabetic loyalty card user.

Further, the objective nutritional guidelines 108 for a loyalty card user may be influenced by the precedence given to each piece of physiological information disclosed in the loyalty card user's physiological information profile. For example, it may be typical for the objective nutritional guidelines 108 to recommend fat free milk as a healthy source of calcium for loyalty card users; however, if lactose intolerance is listed with sufficient precedence in a loyalty card user's physiological information profile, the objective nutritional guidelines 108 may recommend almonds as a source of calcium instead.

In an embodiment, the precedence of a piece of physiological information may determine the magnitude of the piece's effect on the objective nutritional guidelines 108 for the physiological information profile as a whole. In some cases, the pieces of physiological information may have conflicting nutritional recommendations. If that is the case, the piece of physiological information given the most precedence may cause the objective nutritional guidelines 108 to reduce the recommended intake of one or more nutrients and/or foods typically recommended for the physiological characteristic disclosed by the conflicting piece of information, to leave the recommended intake of one or more nutrients and/or foods typically recommended for the physiological characteristic disclosed by the conflicting piece of information unchanged, or to recommend eliminating intake of one or more nutrients and/or foods typically recommended for the physiological characteristic disclosed by the conflicting piece of information. For example, a loyalty card user's physiological information profile may indicate with the highest precedence that the loyalty card user has a history of heart disease and therefore limit or totally eliminate foods with a designated level of saturated fat and/or cholesterol regardless of any other information contained in the loyalty card user's physiological information profile.

The objective nutritional guidelines for food 108 may be maintained in data stores maintained by independent sources but be searchable or accessible from the platform 102. In an embodiment, the objective nutritional guidelines for food 108 may be copied to a memory associated with the platform 102 and updated periodically to keep synchronized with the evolving content in the objective nutritional guidelines for food 108. Hereinafter, the objective nutritional guidelines for food 108 may be referred to as guidelines 108.

The simple nutrition application 114 provides an interface for loyalty card users who have registered to use the simple nutrition application 114 or a related shopping application. The interface may be a web page or other interactive interface that may be remotely accessed by the computer 111 or by the mobile phone 112 that communicates with the network 110 via the base transceiver station 113 that provides a wireless communication link to the mobile phone 112. The loyalty card users may use the interface to plan shopping trips and/or develop a shopping list for their next visit to a store operated by the grocery store or grocery store chain that operates the system 100. Alternatively, the interface may provide an electronic commerce option that allows the loyalty card user to invoke a click to buy functionality to purchase selected products. The loyalty card user may submit payment online and have groceries delivered to his/her place of residence, place of business, or elsewhere.

The simple nutrition application 114 may respond to a request by presenting a list of items that meet nutritional guidelines as captured in the guidelines 108. The list of items that meet nutritional guidelines may be presented in a web page transmitted as a hypertext markup language (HTML) document to the computer 111 or the mobile phone 112. In an embodiment, the simple nutrition application 114 may format and/or configure the HTML document targeted to the mobile phone 112 to be displayed on a typical display of a mobile phone. The list of items may be grouped according to nutrient type and/or food category. For example, beverages that are low in calories may be selected for presentation to the loyalty card user based on an input selecting a nutritional filter of low calories and a food category filter of beverages. For example, beverages that are low in calories but high in vitamin C may be selected for presentation to the loyalty card user that inputs these criteria or filter criteria. The simple nutrition application 114 may provide controls in the user interface for selecting a list member and adding the selected item to an in-progress shopping list. In an embodiment, food category filter criteria may comprise beverages; bread and bakery; breakfast and cereal; cookies, snacks, and candy; dairy, eggs, and cheese; fruits and vegetables; and meat and seafood. In an embodiment, food nutrient filter criteria may comprise calcium, calories, carbohydrates, cholesterol, fiber, fat, iron, iodine, selenium, potassium, protein, saturated fat, sodium, sugar, trans fat, vitamin A, vitamin D, folate, sugar, B vitamins, and vitamin C.

The simple nutrition application 114 may respond to a control input from a loyalty card user to present a list of previously purchased items along with suggested substitutions for these purchased items that are more healthful. The list of previously purchased items may be presented in a web page transmitted as a hypertext markup language (HTML) document to the computer 111 or the mobile phone 112. In an embodiment, the simple nutrition application 114 may format and/or configure the HTML document targeted to the mobile phone 112 to be displayed on a typical display of a mobile phone. The list of previously purchased items may be determined based on a frequency of purchase or some other selective basis. The list may be analyzed, for example by the purchase history analyzer 116, to determine the least healthy previously purchased items and to list these items in order of the least to the most healthy previously purchased items, for example based on the guidelines 108. Alternatively, the least healthy previously purchased items may be identified based at least in part on a nutritional goal defined by the loyalty account user. Alternatively, the least healthy previous purchases may be presented in some other distinctive way to call attention to it. In this way, the least healthy items may be most immediately brought to the attention of the loyalty card user, for example at the top of a display window. In an embodiment, the 30 most offensive items are selected for listing. Alternatively, the 20 most offensive items are selected for listing or the 10 most offensive items are selected for listing. Alternatively, some other number of most offensive items are selected for listing. In an embodiment, the number of items selected for listing may be based on whether the loyalty card user is using the computer 111 or the mobile phone 112 to interact with the simple nutrition application 114. For example, fewer items may be selected for listing when the loyalty card user is using the mobile phone 112 that may have a smaller display than the display associated with the computer 111.

The substitution generator 118 may analyze the list of least healthy previously purchased items, identify candidate purchase items from the same food categories by accessing the product data store 106, analyze the candidate purchase items based on the guidelines 108, and determine food substitution recommendations that provide the best improvement in healthy qualities over the unhealthy previously purchased items. For example, a turkey bacon substitution may be suggested for a previous pork bacon purchase. For example, a low calorie fruit juice may be suggested as a substitute for a high calorie carbonated soft drink. One or more of the healthy substitution candidates may be presented proximate to the unhealthy previously purchased items, and the interface may promote the loyalty card user to select from the healthy substitution candidates to add to the in-progress shopping list. In an embodiment, substitute candidates that are associated with an individual discount targeted to the loyalty card user may be presented distinctively to alert the loyalty card user and/or call attention to the available discount. The substitutes may be presented in a web page transmitted as a hypertext markup language (HTML) document to the computer 111 and/or the mobile phone 112.

In an embodiment, the purchase history analyzer 116 may analyze a most recent purchases associated with a loyalty card user over a predefined duration of time or time period by accessing the purchase data store 104 to generate a nutrition history. For example, the nutrition history may determine an average daily consumption of nutrients over the subject most recent time period, compare the average daily consumption of nutrients to the guidelines 108, and provide a roll-up summary or report card of how well the loyalty card user's food consumption matches to or meets nutrition guidelines. In an embodiment, the interface provided by the simple nutrition application 114 may provide controls for identifying how many household members consume the food purchases and a distribution among the household members. For example, a household may comprise an adult male, an adult female, a 10 year old male child, and an 8 year old female child. For example, the loyalty card user may define a food distribution to be 35% adult male, 30% adult female, 20% male child, 15% female child. These distributions may be used along with the household purchasing data to determine a nutritional report card for each household member.

In an embodiment, the simple nutrition application 114 and/or the filtering application 120 may promote the loyalty card user inputting a food category filter criteria and one or more food nutrient filter criteria. The substitution generator 118 may then generate substitution suggestions for previously purchased items belonging to the input food category filter criteria based on the one or more food nutrient filter criteria. Thus, if the food category is cereal and the nutrient filter criteria comprise high protein and low carbohydrate, the substitution generator 118 searches the product data store 106 for cereal products that meet the two food nutrient filter criteria and presents one or more candidate substitutes that best match the food nutrient filter criteria.

In an embodiment, the simple nutrition application 114 and/or the filtering application 120 may promote the loyalty card user inputting a food attribute filter criteria in addition to the food category filter criteria and the one or more food nutrient filter criteria. Food attributes may comprise carbohydrate amounts/values/equivalents (hereinafter "Carb Choices") as discussed hereinbelow, heart healthy, gluten-free, Weight Watchers® points, immune boosting, allergen information, organic, anti-inflammatory, low glycemic index, lower cholesterol, probiotic, all natural, kosher, fresh, locally grown, good source of potassium, good source of protein, good source of vitamin A, good source of iron, good source of iodine, good source of selenium, made with whole grains, sodium smart, good source of folate, good source of calcium, good source of vitamin C, good source of vitamin D, good source of B vitamins, low fat, fat free, low saturated fat, 100% juice, good source of antioxidants, low sodium, good source of fiber, 0 g trans fat, calorie smart, sugar free and/or other food attributes. Further, food attributes may be determined by a set standard, e.g. low glycemic index is determined based on an accepted definition value of low glycemic index, or food attributes may be determined by selecting a desired quantity e.g. three Weight Watchers® points or two Carb Choices.

Allergies to milk, peanuts, tree and/or other nuts, shellfish, eggs, and soy are common food allergies. Allergen information about these and/or other allergens may be included in the list of food attributes. Allowing the loyalty card user to select from food attributes may assist loyalty card users with diabetes, heart disease, allergies and/or other medical conditions in finding foods that align with nutrition recommendations for those medical conditions. In order to facilitate easier identification and location, food attributes may be listed on in-store tags, labels, signs, or in other locations configured to assist the loyalty card user in locating items with a given food attribute.

For example, a loyalty card user may be a diabetic. Diabetes is a metabolic disease in which the affected person has an insulin deficiency resulting in a reduced ability to adjust blood sugar levels. Carbohydrates are a nutrient source that when digested cause blood sugar levels to rise. Maintaining stable blood sugar levels is an important concern for diabetics, and regulating carbohydrate intake is one way of controlling those levels. The ability to select Carb Choices among the list of food attribute filter criteria may assist the diabetic loyalty card user in building a suitable shopping list. Carb Choices are a unit of nutritional measurement, wherein approximately 11-20 grams of carbohydrates is equivalent to one Carb Choice. In an embodiment, 15 grams of carbohydrates may be equivalent to one Carb Choice. Carb Choices may be calculated and applied to foods offered by the grocery store or grocery store chain that operates the system 100. The diabetic loyalty card user may find it more convenient to keep track of Carb Choices than to keep track of total carbohydrates, thus selecting Carb Choices as the food attribute filter criteria may save the diabetic loyalty card user time and effort in finding food items with a desired level of carbohydrates. As discussed above, the diabetic loyalty card user's physiological characteristics may affect his/her recommended carbohydrate intake. The objective nutritional guidelines 108 may be applied to Carb Choices in a manner substantially similar to that described above. Alternatively, the loyalty card user may decide his/her own carbohydrate intake independently and choose Carb Choices accordingly.

The substitution generator 118 may generate suggestions for items belonging to the input food category filter criteria based on the one or more food nutrient filter criteria and the food attribute filter criteria. Thus, if the food category is cereal, the nutrient filter criteria comprise high protein and low carbohydrate, and the food attribute filter criterion is heart healthy the substitution generator 118 searches the product data store 106 for heart healthy cereal products that meet the two food nutrient filter criteria and presents one or more candidate substitutes that best match the food nutrient filter criteria and the food attribute filter criteria.

In an embodiment, a loyalty card user may request the simple nutrition application 114 to generate a shopping list. The simple nutrition application 114 may respond by presenting a list of items that meet personalized nutritional guidelines as captured in the objective nutritional guidelines 108 based on the loyalty card user's physiological information profile stored in the physiological information profile data store 105. The list may be presented in a manner substantially similar to that described hereinabove.

Alternatively, the simple nutrition application 114 may respond to a control input from a loyalty card user to present a list of previously purchased items along with suggested substitutions for these purchased items that are more healthful. The list of previously purchased items may be identified and presented in a manner substantially similar to that described herein above. Substitutions for previously purchased items may be identified by the substitution generator 118 by analyzing the list of previously purchased items based on the objective nutritional guidelines 108 set forth for one or more physiological characteristics disclosed in the loyalty card user's physiological information profile and selecting candidate item substitutes that better satisfy the objective nutritional guidelines 108.

As the loyalty card user builds a shopping list, he or she may store the in-progress shopping list and complete the list at a later time. The loyalty card user may have a completed shopping list emailed to the computer 111 or to the mobile phone 112. The loyalty card user may have the completed shopping list texted to the mobile phone 112.

In an embodiment, the nutritional management system 100 may be configured to implement quick response codes. A quick response code that links to nutritional information, nutritional guidelines, the SimpleNutrition management platform 102, a retailer webpage, a loyalty card user shopping history, and/or to something else may be placed on products, in advertisements, and/or placed elsewhere. In an embodiment, a loyalty card user may scan a quick response code on an advertisement with the mobile phone 112 and be directed to a grocery store website. Scanning the quick response code may allow the loyalty card user to create the shopping list while the advertisement is fresh in mind. Once at the website, the loyalty card user may create a shopping list as described hereinabove.

Figure 2:
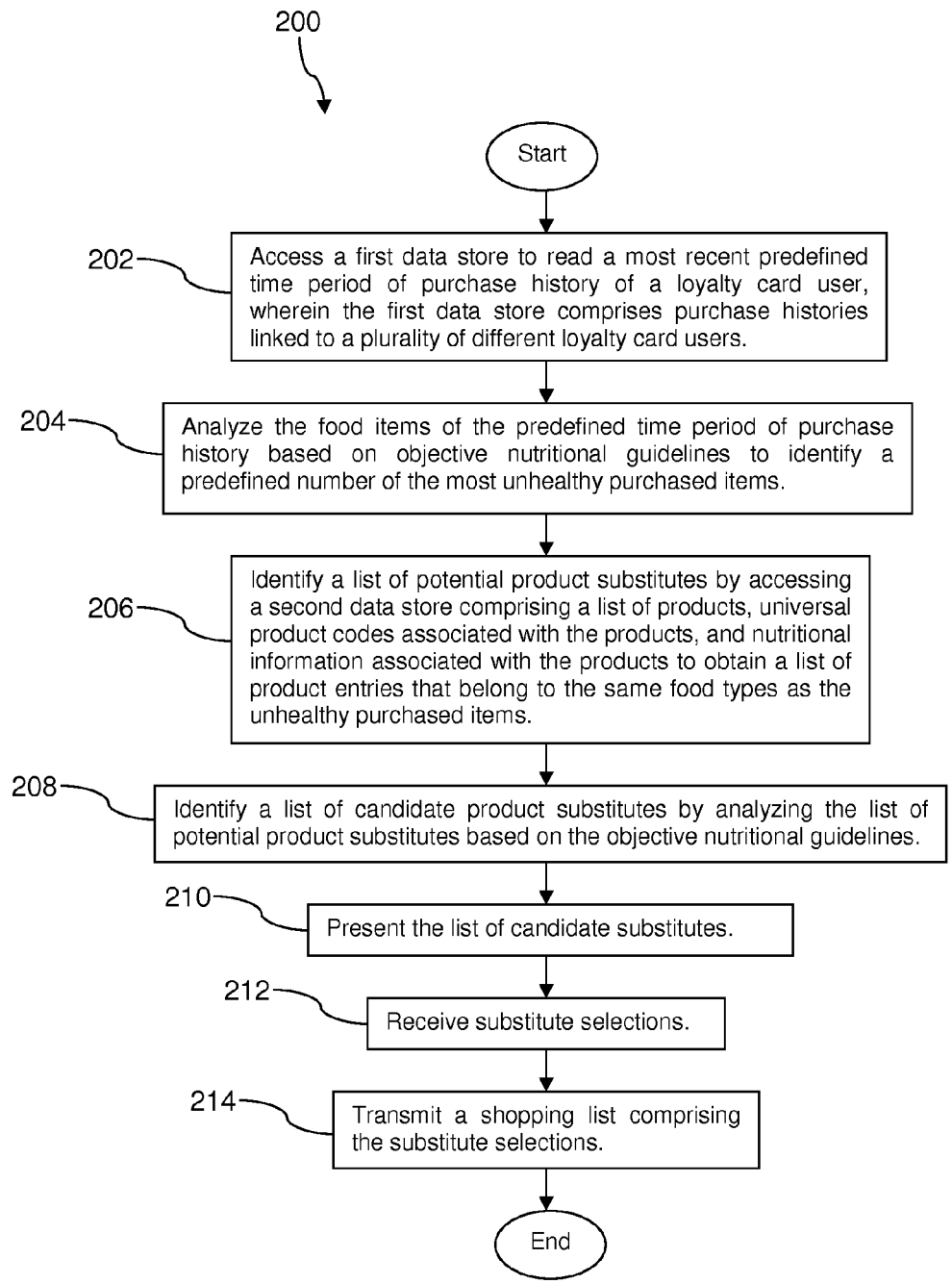
FIG. 2 is a flow chart of a method according to an embodiment of the disclosure.

Turning now to FIG. 2, a method 200 is described. At block 202, access a first data store to read a most recent predefined time duration of purchase history of a loyalty card user, wherein the first data store comprises purchase histories linked to a plurality of different loyalty card users. In an embodiment, the first data store comprises the purchase data store 104 described above with reference to FIG. 1. At block 204, analyze the food items of the most recent predefined time duration of purchase history based on objective nutritional guidelines to identify a predefined number of the most unhealthy purchased items, for example the most 3 months of purchase history, the most recent 6 months of purchase history, or some other time interval. The predefined time duration need not be an integer number of months but may be a number of days, a number of weeks, or some other time unit. In an embodiment, the objective nutritional guidelines may be obtained from the objective nutritional guidelines 108 described with reference to FIG. 1. At block 206, identify a list of potential product substitutes by accessing a second data store comprising a list of products, universal product codes associated with the products, and nutritional information associated with the products to obtain a list of product entries that belong to the same food types as the unhealthy purchased items. The second data store may further comprise product shelf price and/or promotion price information. In an embodiment, the second data store comprises the data store 106 described above with reference to FIG. 1. At block 208, identify a list of candidate product substitutes by analyzing the list of potential product substitutes based on the objective nutritional guidelines. At block 210, present the list of candidate substitutes. The candidate substitutes may be presented along with their corresponding pricing information. In an embodiment, the pricing information for the candidate substitute products may be compared to the pricing information for the products they are intended to substitute for. At block 212, receive substitute selections. At block 214, transmit a shopping list comprising the substitute selections. In an embodiment, the method 200 may be performed by the platform 102 described with reference to FIG. 1. The method 200 may provide an easy way to manage household nutrition and promote more healthy eating.

Figure 3:
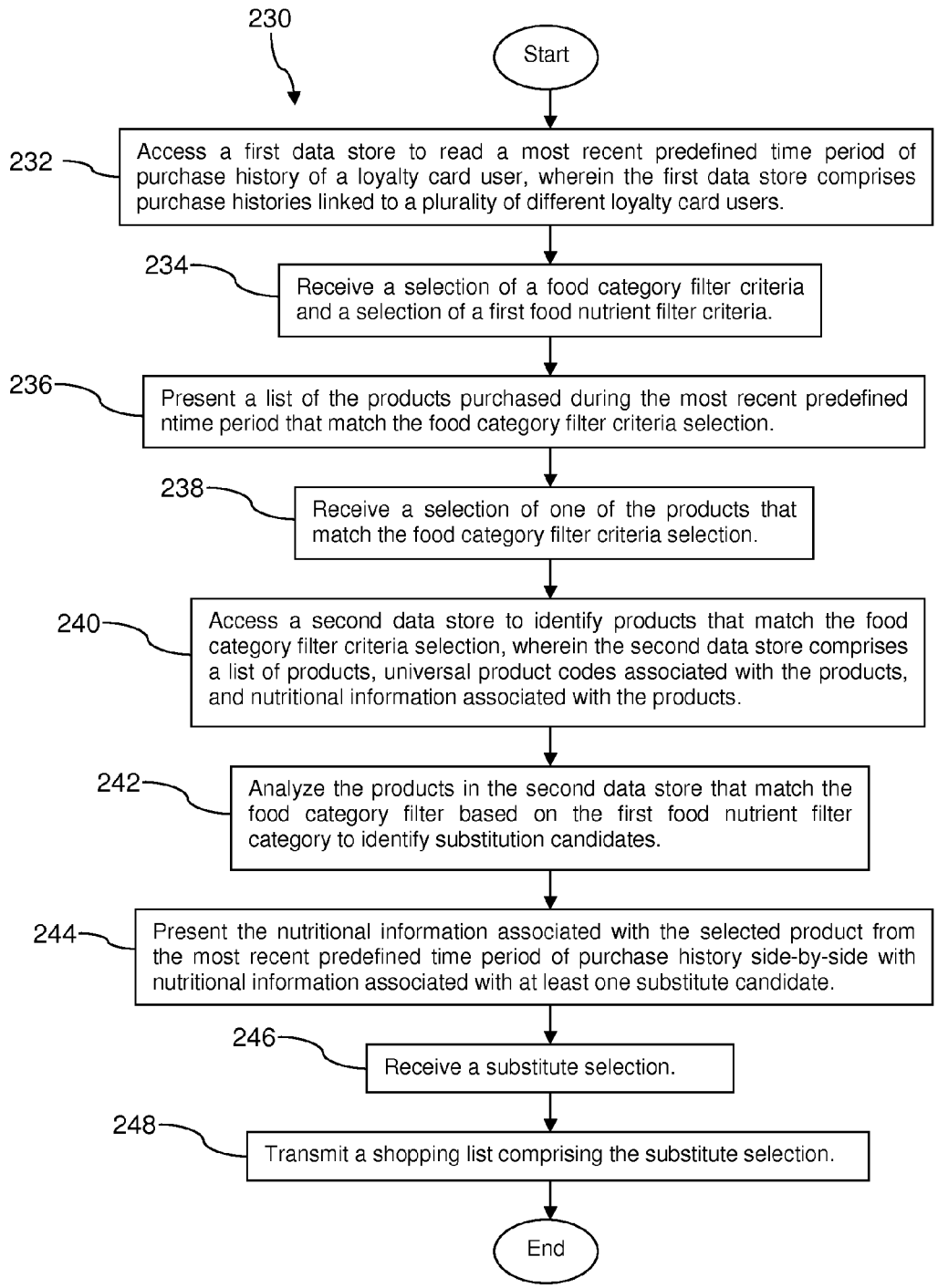
FIG. 3 is a flow chart of another method according to an embodiment of the disclosure.

Turning now to FIG. 3, a method 230 is described. At block 232, access a first data store to read a most recent predefined time period of purchase history of a loyalty card user, wherein the first data store comprises purchase histories linked to a plurality of different loyalty card users, for example the most recent 3 months, 6 months, or some other time duration. The predefined time duration need not be an integer number of months but may be a number of days, a number of weeks, or some other time unit. In an embodiment, the first data store comprises the purchase data store 104 described above with reference to FIG. 1. At block 234, receive a selection of a food category filter criteria and a selection of a first food nutrient filter criteria. At block 236, present a list of the products purchased during the most recent predefined time duration that match the food category filter criteria selection. At block 238, receive a selection of one of the products that match the food category filter criteria selection. At block 240, access a second data store to identify products that match the food category filter criteria selection, wherein the second data store comprises a list of products, universal product codes associated with the products, and nutritional information associated with the products. In an embodiment, the second data store comprises the product data store 106 described with reference to FIG. 1. At block 242, analyze the products in the second data store that match the food category filter based on the first food nutrient filter category to identify substitution candidates. At block 244, present the nutritional information associated with the selected product from the most recent predefined time period of purchase history side-by-side with nutritional information associated with at least one substitute candidate. At block 246, receive a substitute selection. For example, the nutritional information may be presented on a display associated with the computer 111 or the mobile phone 112. At block 248, transmit a shopping list comprising the substitute selection. Portions of the method 230 may be performed by the platform 102.

Figure 4:
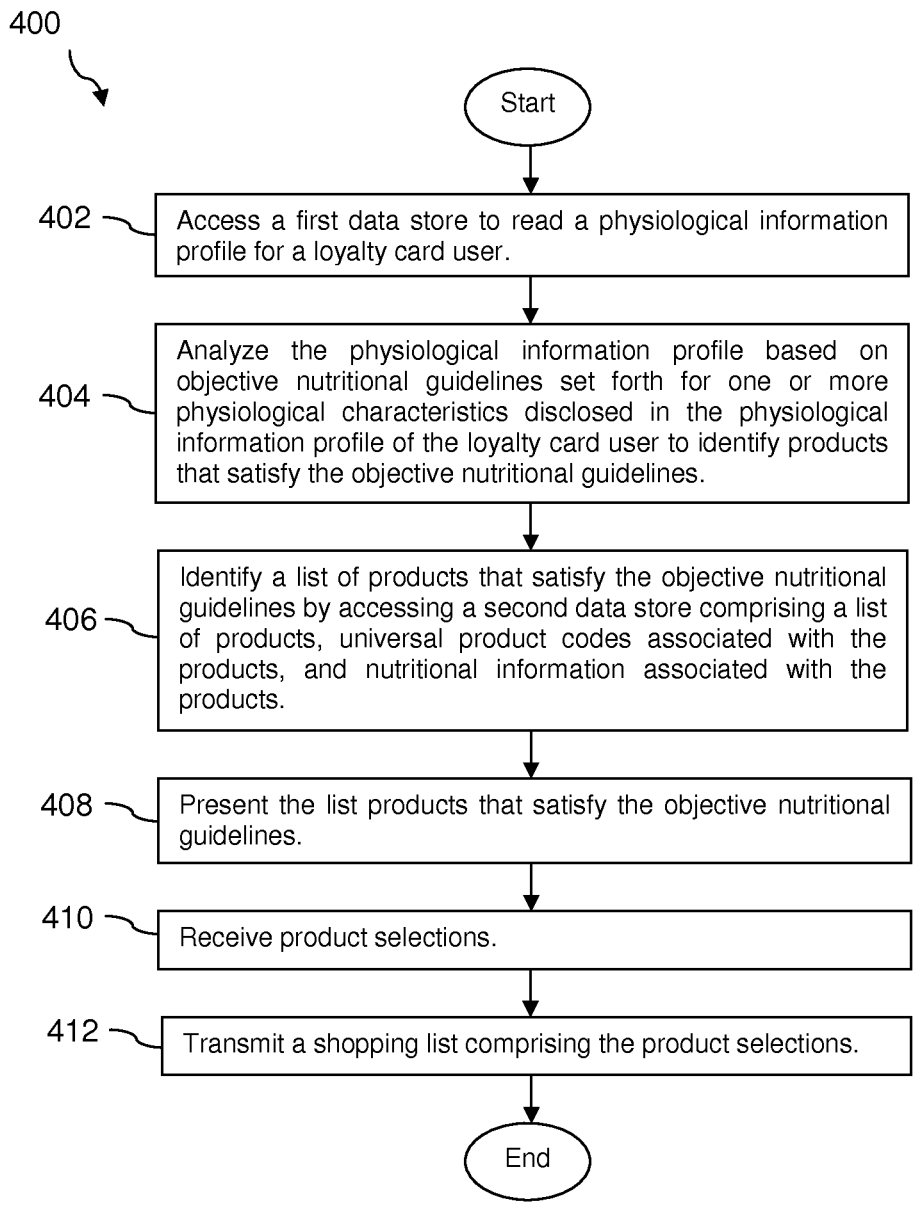
FIG. 4 is a flow chart of another method according to an embodiment of the disclosure.

Turning now to FIG. 4, a method 400 is described. At block 402, a first data store may be accessed to read a physiological information profile for a loyalty card user. In an embodiment, the first data store may comprise the physiological information profile data store 105 discussed with reference to FIG. 1. The physiological information profile is analyzed based on objective nutritional guidelines set forth for one or more physiological characteristics disclosed in the physiological information profile of the loyalty card user at block 404. The analysis may be used to identify products that satisfy the objective nutritional guidelines. In an embodiment, products that satisfy the objective nutritional guidelines in light of prescription medication that the loyalty card user is taking may be identified by the analysis. As discussed above with reference to FIG. 1, pieces of physiological information contained in the physiological information profile may be afforded different levels of precedence. At block 406, a list of products that satisfy the objective nutritional guidelines may be identified by accessing a second data store comprising a list of products, universal product codes associated with the products, and nutritional information associated with the products. In an embodiment, medical conditions comprising at least on of diabetes, heart disease, cancer, Crohn's disease, ulcers, hemophilia, viral infections, bacterial infections, fungal infections, and other medical conditions may be given precedence over physical characteristics comprising at least one of height, sex, and race when identifying the list of products that satisfy the objective nutritional guidelines. The second data store may comprise the product data store 106 described with reference to FIG. 1. The list of products that satisfy the objective nutritional guidelines may be presented at block 408. Product selections may be received at block 410. At block 412, a shopping list comprising the product selections may be transmitted.

In an embodiment, the method 400 may further comprise accessing a third data store to read a most recent predefined time period of purchase history of the loyalty card user, wherein the third data store comprises purchase histories linked to a plurality of different loyalty card users. The food items of the most recent predefined time period of purchase history may be analyzed based on objective nutritional guidelines set forth for one or more physiological characteristics disclosed in the physiological information profile of the loyalty card user to identify a predefined number of the most unhealthy purchased items. A list of potential product substitutes may be identified by accessing the second data store comprising a list of products, universal product codes associated with the products, and nutritional information associated with the products to obtain a list of product entries that belong to the same food types as the unhealthy purchased items. A list of candidate product substitutes may be identified by analyzing the list of potential product substitutes based on the objective nutritional guidelines. The list of candidate substitutes may be presented, substitute selections may be received, and a shopping list comprising the substitute selections may be transmitted in a manner substantially similar to that described hereinabove with reference to FIG. 1.

In an embodiment, the method 400 may be implemented by a computer system configured to allow a loyalty card user to generate a healthy shopping list based on personalized nutrition recommendations. As discussed above with reference to the objective nutritional guidelines 108 of FIG. 1, objective nutritional guidelines may take into account physiological characteristics disclosed in the loyalty card user's physiological information profile. Thus, the objective nutritional guidelines may be different, e.g. personalized, for different loyalty card users. The objective nutritional guidelines for the medical conditions comprising at least one of diabetes, heart disease, cancer, Crohn's disease, ulcers, hemophilia, viral infections, bacterial infections, fungal infections, and other medical conditions may be personalized to the loyalty card user by taking into account the loyalty card user's physical characteristics comprising at least one of height, weight, race, sex, age, body fat percentage, BMI, caloric expenditure, or allergies when establishing the objective nutritional guidelines.

Figure 5:
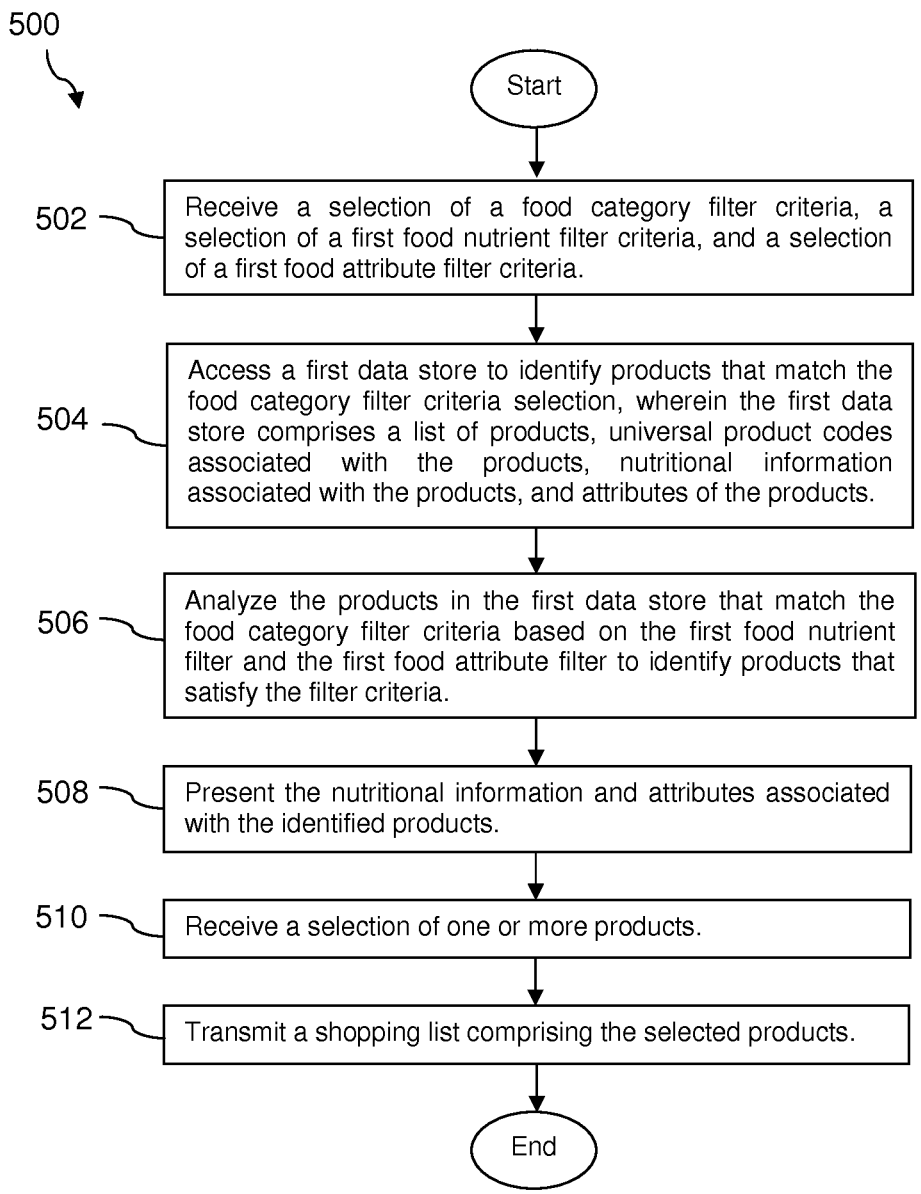
FIG. 5 is a flow chart of another method according to an embodiment of the disclosure.

Turning now to FIG. 5, a method 500 is described. At block 502, a selection of a food category filter criteria, a selection of a first food nutrient filter criteria, and a selection of a first food attribute filter criteria may be received. A first data store may be accessed at block 504 to identify products that match the food category filter criteria selection, wherein the first data store comprises a list of products, universal product codes associated with the products, nutritional information associated with the products, and attributes of the products. In an embodiment, the first data store may comprise the product data store 106 as discussed with reference to FIG. 1. At block 506, the products in the first data store that match the food category filter criteria may be analyzed based on the first food nutrient filter and the first food attribute filter to identify products that satisfy the filter criteria. The nutritional information and attributes associated with the identified products may be presented at block 508. A selection of one or more products may be received at block 510. A shopping list comprising the selected products may be transmitted at block 512.

In an embodiment, the method 500 may further comprise accessing a second data store to read a most recent predefined time period of purchase history of a loyalty card user, wherein the second data store comprises purchase histories linked to a plurality of different loyalty card users. A list of candidate product substitutes may be identified by analyzing the purchase history based on the first food nutrient filter and the first food attribute filter to identify products that satisfy the filter criteria. Nutritional information and attributes of products on the list of candidate substitutes may be presented in a manner substantially similar to that described hereinabove with reference to FIG. 1.

In an embodiment, the method 500 may further comprise accessing a third data store to read a physiological information profile for the loyalty card user. The physiological information profile may be analyzed based on objective nutritional guidelines set forth for one or more physiological characteristics disclosed in the physiological information profile of the loyalty card user to identify products that satisfy the objective nutritional guidelines, the food category filter criteria, the first food nutrient filter criteria, and the first food attribute filter criteria. A list of products that satisfy the objective nutritional guidelines, the food category filter criteria, the first food nutrient filter criteria, and the first food attribute filter criteria may be identified by accessing the first data store comprising a list of products, universal product codes associated with the products, and nutritional information associated with the products.

The method 500 may be implemented by a computer system configured to allow a loyalty card user to create a healthy shopping list. The loyalty card user may interact with an application that may be performing the method 500 through an interface as described hereinabove with reference to FIG. 1. In an embodiment, the loyalty card user may access the computer system implementing the method 500 to create a shopping list. The loyalty card user may use personal knowledge of his/her physiological characteristics to select food category filter criteria, food nutrient filter criteria, and/or food attribute filter criteria. Alternatively, physiological information contained in the loyalty card user's physiological information profile may be used to generate recommended food category filter criteria, food nutrient filter criteria, and/or food attribute filter criteria to be presented to the loyalty card user. Food attribute criteria may comprise Carb Choices, heart healthy, gluten-free, Weight Watchers® points, allergen information, immune boosting, organic, low glycemic index, lower cholesterol, probiotic, all natural, kosher, fresh, locally grown, anti-inflammatory, good source of potassium, good source of protein, good source of vitamin A, good source of iron, good source of iodine, good source of selenium, made with whole grains, sodium smart, good source of folate, good source of calcium, good source of vitamin C, good source of vitamin D, good source of B vitamins, low fat, fat free, low saturated fat, 100% juice, good source of antioxidants, low sodium, good source of fiber, 0 g trans fat, calorie smart, sugar free, and/or other food attributes.

For example, a diabetic loyalty card user may access the computer system implementing the method 500 and select cereals from the food category filter criteria, high protein from the food nutrient filter criteria, and two Carb Choices from the food attribute filter criteria. In response, cereals may be presented that satisfy the food nutrient filter criteria and food attribute filter criteria. The cereals may be presented in order according to how well they satisfy the filter criteria. The diabetic loyalty card user may select the plurality of filter criteria according to his/her personal nutritional decisions, or the diabetic loyalty card user may select from a plurality of filter criteria suggested by the objective nutritional guidelines set forth for the diabetic loyalty card user's physiological information profile. Selecting food attribute filter criteria in addition to food category and food nutrition filter criteria may assist loyalty card users in finding healthy foods whose benefits may not be immediately apparent. For example, selecting anti-inflammatory foods may make it easier to find foods with anti-inflammatory characteristics, such as high omega-3 fatty acid content, that may be difficult to determine from other nutritional information.

Figure 6:
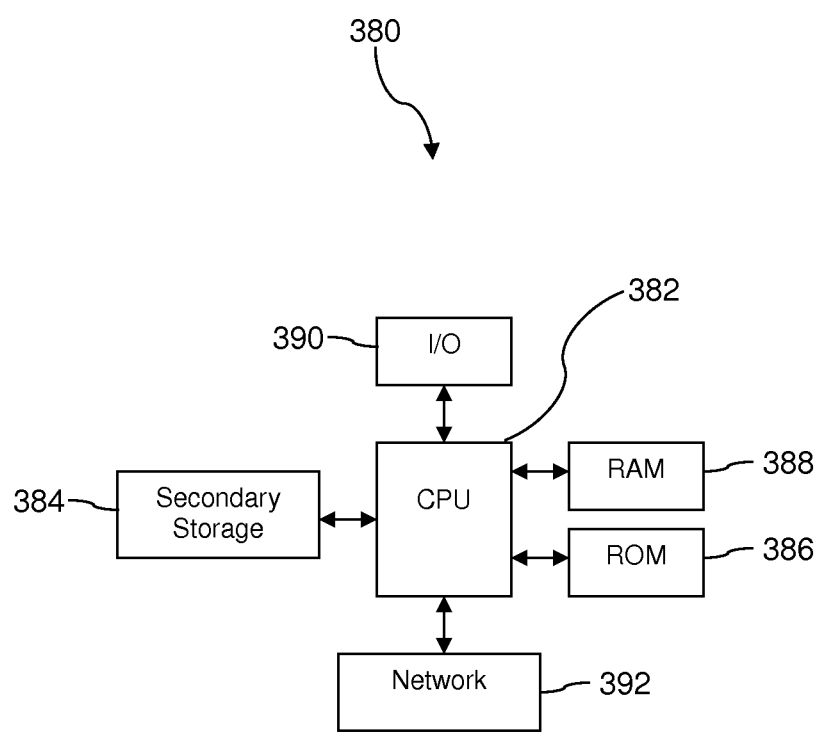
FIG. 6 is a block diagram of a computer system according to an embodiment of the disclosure.

FIG. 6 illustrates a computer system 380 suitable for implementing one or more embodiments disclosed herein. For example, the SimpleNutrition Management Platform 102 may be implemented in a form substantially similar to that of the computer system 380. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well known to one skilled in the art. The baseband signal and/or signal embodied in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A nutritional management system, comprising:
   a plurality of processors in a cloud computing environment;
   a memory of ROM, RAM, or both ROM and RAM located in the cloud computing environment;
   a first data store comprising a physiological information profile for each of a plurality of different loyalty card users;
   a second data store comprising a list of products, universal product codes associated with the products, and nutritional information associated with the products;
   a third data store comprising purchase histories linked to the plurality of different loyalty card users; and
   an application stored and partitioned in the memory that, when executed by the plurality of processors,
      accesses the first data store to read the physiological information profile of a loyalty card user,
      analyzes the physiological information profile of the loyalty card user based on objective nutritional guidelines set forth for one or more physiological characteristics disclosed in the physiological information profile of the loyalty card user,
      accesses the third data store to read a purchase history of the loyalty card user over a most recent predefined time period,
      analyzes the most recent predefined time period of the purchase history of the loyalty card user based on objective nutritional guidelines set forth for one or more of the physiological characteristics disclosed in the physiological information profile of the loyalty card user to identify unhealthy purchased items, wherein the unhealthy purchased items includes a least healthy previous purchase,
      searches the second data store to find substitute candidates for the unhealthy purchased items,
      identifies at least one of the substitute candidates that is eligible for an individual discount targeted to the loyalty card user,
      transmits, in a webpage to a mobile phone of the loyalty card user via a network connected to a wireless communication link provided by a transceiver base station, the least healthy previous purchase, the at least one of the substitute candidates that is eligible for the individual discount, and the individual discount,
      wherein the least healthy previous purchase, the at least one of the substitute candidates that is eligible for the individual discount, and the individual discount are presented in the web page to call attention to the least healthy previous purchase and the individual discount for the at least one of the substitute candidates that is eligible for the individual discount,
      receives a selection, from the mobile phone via the network connected to the wireless communication link provided by the transceiver base station, of one or more of the substitute candidates that is eligible for the individual discount, and
      generates a personalized shopping list comprising the one or more of the substitute candidates that is selected and that is based on the loyalty card user's physiological information profile.

2. The system of claim 1, wherein the objective nutritional guidelines for at least one of the physiological characteristics described in the physiological information profile takes precedence over the objective nutritional guidelines for other of the physiological characteristics described in the physiological information profile when the application searches the second data store to find products that satisfy the objective nutritional guidelines.

3. The system of claim 1, wherein when executed by the plurality of processors, the application further:
   searches the second data store to find products that satisfy the objective nutritional guidelines, and
   receives, from the mobile phone via the network connected to the wireless communication link provided by the transceiver base station, a selection of one or more of the products, wherein the personalized shopping list further comprises selected products that are based on the loyalty card user's physiological information profile.

4. The system of claim 1, wherein the loyalty card user's physiological information profile comprises information about one or more of the loyalty card user's height, weight, race, sex, age, body fat percentage, BMI, caloric expenditure, organs, history of injuries, history of illness, allergies, immune system; family medical history, personal medical history, current medical condition, addictions, dental health, gastrointestinal health, mental health, joint health, cardiovascular health, respiratory health, hormone activity, history of infection, history of disease, information about medication that the loyalty card user is taking, or information about another aspect of the loyally card user's physiological characteristics.

5. The system of claim 1, wherein the nutritional information comprises information indicating the quantity of at least one of calories, protein, carbohydrate, fat, saturated fat, trans fat, fiber, sodium, potassium, calcium, iron, iodine, selenium, cholesterol, vitamin A, vitamin C, folate, sugar contained in the products, or combinations thereof.

6. A method performed by an application executed by a plurality of processors in a cloud computing environment, comprising:
accessing, by the plurality of processors, a first data store to read a physiological information profile for a loyalty card user;
analyzing, by the plurality of processors, the physiological information profile based on objective nutritional guidelines set forth for one or more physiological characteristics disclosed in the physiological information profile of the loyalty card user;
accessing, by the plurality of processors, a third data store to read a most recent predefined time period of a purchase history of the loyalty card user, wherein the third data store comprises purchase histories linked to a plurality of different loyalty card users;
analyzing, by the plurality of processors, the most recent predefined time period of the purchase history of the loyalty card user based on objective nutritional guidelines set forth for one or more of the physiological characteristics disclosed in the physiological information profile of the loyalty card user to identify unhealthy purchased items, wherein the unhealthy purchased items includes a least healthy previous purchase,
searching, by the plurality of processors, a second data store to find substitute candidates for the unhealthy purchased items, wherein the second data store comprises products, universal product codes associated with the products, and nutritional information associated with the products,
identifying, by the plurality of processors, at least one of the substitute candidates that is eligible for an individual discount targeted to the loyalty card user,
transmitting, by the plurality of processors in a web page to a mobile phone of the loyalty card user via a network connected to a wireless communication link provided by a transceiver base station, the least healthy previous purchase, the at least one of the substitute candidates that is eligible for the individual discount, and the individual discount,
wherein the least healthy previous purchase, the at least one of the substitute candidates that is eligible for the individual discount, and the individual discount are presented in the web page to call attention to the least healthy previous purchase and the individual discount for the at least one of the substitute candidates,
receiving, by the plurality of processors from the mobile phone via the network connected to the wireless communication link provided by the transceiver base station, a selection of one or more of the substitute candidates that is eligible for the individual discount, and
generating, by the plurality of processors, a personalized shopping list comprising the one or more substitute candidates that is selected and that is based on the loyalty card user's physiological information profile.

7. The method of claim 6, further comprising:
identifying, by the plurality of processors, a list of products that satisfy the objective nutritional guidelines by accessing the second data store;
wherein precedence is given to at least one of the physiological characteristics described in the physiological information profile over others of the physiological characteristics described in the physiological information profile when identifying the list of products that satisfy the objective nutritional guidelines.

8. The method of claim 6, wherein the physiological information profile comprises information about one or more of the loyalty card user's height, weight, race, sex, age, body fat percentage, BMI, caloric expenditure, organs, history of injuries, history of illness, allergies, immune system, family medical history, personal medical history, current medical condition, addictions, dental health, gastrointestinal health, mental health, joint health, cardiovascular health, respiratory health, hormone activity, history of infection, history of disease, information about medication the loyalty card user is taking, or information about another aspect of the loyalty card user's physiological characteristics.

9. The method of claim 6, wherein the physiological information profile comprises information supplied by the loyalty card user.

10. The method of claim 7, wherein the physiological characteristics comprising at least one of diabetes, heart disease, cancer, Crohn's disease, ulcers, hemophilia, viral infections, bacterial infections, fungal infections, and other medical conditions are given precedence over physiological characteristics comprising at least one of height, sex, and race when identifying a list of products that satisfy the objective nutritional guidelines.

11. The method of claim 6, further comprising:
assigning, by the plurality of processors, a relative importance to each piece of physiological information contained in the physiological information profile.

12. The method of claim 6, wherein the objective nutritional guidelines for medical conditions comprising at least one of diabetes, heart disease, cancer, Crohn's disease, ulcers, hemophilia, viral infections, bacterial infections, fungal infections, and other medical conditions are personalized to the loyalty card user by taking into account the loyalty card user's physical characteristics comprising at least one of height, weight, race, sex, age, body fat percentage, BMI, caloric expenditure, or allergies when establishing the objective nutritional guidelines.

* * * * *